United States Patent [19]
Butler

[11] Patent Number: 5,985,326
[45] Date of Patent: Nov. 16, 1999

[54] METHOD OF PRODUCING A SOLID DISPERSION OF A POORLY WATER SOLUBLE DRUG

[75] Inventor: James Matthew Butler, Romford, United Kingdom

[73] Assignee: ICOS Corporation, Bothell, Wash.

[21] Appl. No.: 08/952,938

[22] PCT Filed: May 30, 1996

[86] PCT No.: PCT/EP96/02299

§ 371 Date: Feb. 6, 1998

§ 102(e) Date: Feb. 6, 1998

[87] PCT Pub. No.: WO96/38131

PCT Pub. Date: Dec. 5, 1996

[30] Foreign Application Priority Data

Jun. 2, 1995 [GB] United Kingdom .................. 9511220

[51] Int. Cl.⁶ ............................. A61K 9/10; A61K 47/32; A61K 47/38
[52] U.S. Cl. .......................... 424/484; 424/486; 424/487; 424/488
[58] Field of Search ...................................... 424/484, 468, 424/457, 486–488; 514/781, 772.6

[56] References Cited

U.S. PATENT DOCUMENTS

5,194,263  3/1993  Chamberlain et al. .
5,665,331  9/1997  Bagchi et al. .

FOREIGN PATENT DOCUMENTS

0 297 866     6/1988  European Pat. Off. .......... A61K 9/20
0 558 104 A1  1/1993  European Pat. Off. ...... C07D 243/12
WO 95/19978   7/1995  WIPO .......................... C07D 471/14

*Primary Examiner*—Edward J. Webman
*Attorney, Agent, or Firm*—Marshall, O'Toole, Gerstein, Murray & Borun

[57] ABSTRACT

Solid dispersions of poorly soluble drugs, such as (6R, 12aR)-2,3,6,7,12,12a-hexahydro-2-methyl-6-(3,4-methylenedioxyphenyl)-pyrazino[2',1':6,1]pyrido[3,4-b]indole-1,4-dione and (+)-N-[1-(adamantanmethyl)-2,4-dioxo-5-phenyl-2,3,4,5-tetrahydro-1H-1,5-benzodiazepin-3-yl]-N'-phenylurea, methods of preparing the solid dispersions, and use of the solid dispersions in pharmaceutical compositions are disclosed.

28 Claims, No Drawings

METHOD OF PRODUCING A SOLID DISPERSION OF A POORLY WATER SOLUBLE DRUG

The present invention relates to the field of solid dispersions of poorly water soluble drugs, to processes for their preparation and their use in pharmaceutical compositions. More particularly the present invention relates to solid dispersions in the form of co-precipitates of poorly water soluble drugs and their compositions with a pharmaceutically acceptable carrier or excipient therefor. Specifically, the invention relates to co-precipitates of (a) a potent and selective inhibitor of cyclic guanosine 3',5'-monophosphate specific phosphodiesterase (cGMP specific PDE) and (b) a potent and selective gastrin and CCK B antagonist, processes for the preparation of such solid dispersions, pharmaceutical compositions containing the same and their use thereof in therapy.

Co-precipitation is a recognised technique for increasing the dissolution of poorly water soluble drugs, such as griseofulvin, ketoprofen, sulphathiazide, spirinolactone, tolbutamide and nifedipine, so as to consequently improve bioavailability thereof. Techniques such as solvent deposition, lyophilization, solvate formation and solid dispersion (of which co-precipitation is an example as described above) have therefore been developed to try to overcome the problem of poor water solubility and resultant low bioavailability.

Solid dispersions in the pharmaceutical field are dispersions of one or more active ingredients, generally poorly water soluble drugs, in an inert carrier or matrix at solid state, which are prepared by either melting the two (fusion), or dissolving them in a solvent, or a combination of approaches, followed by removal of the solvent.

Manufacture of pharmaceutical dispersions by the above referred to melting or fusion technique, involves fusion of the two components where the drug and the carrier are allowed to melt at temperatures at or above the melting point of both the drug and carrier. In the fusion process, the drug and carrier are first blended and both melted in a suitable mixer. The molten mixture is then cooled rapidly to provide a congealed mass which is subsequently milled to produce a powder. The fusion process is technically simple provided that the drug and carrier are miscible in the molten state but this is not always the case and furthermore, the process is limited in that it tends to lead to drug decomposition due to the high temperatures required to melt the two components.

The solvent-based process uses organic solvents to dissolve and intimately disperse the drug and carrier molecules. Identification of a common solvent for both drug and carrier can be problematic, and complete solvent removal from the product can be a lengthy process. In addition, large volumes of solvents are generally required which can give rise to toxicological problems. The drug and carrier are typically dissolved in a solvent such as methylene chloride, acetone, ethanol and mixtures thereof and the solvent is later removed by precipitation techniques, evaporation or the like, while the drug/carrier solid dispersion is collected as a powdered mass.

In the case where there is difficulty with thermal instability and immiscibility between the drug and the carrier, the hybrid fusion-solvent method can be employed. The drug is first dissolved in a small quantity of organic solvent and added to the molten carrier. The solvent is then evaporated to generate a product that is subsequently milled to produce a powder. The pharmacokinetics, dissolution rates and processes for formulation of many different solid pharmaceutical dispersions is discussed at length in an article by Ford J., in Pharm. Acta. Helv. 61, 3; 69–88 (1986).

Co-precipitation techniques employ the use of an organic solvent or solvents to dissolve and intimately disperse the drug and carrier molecules as hereinbefore described. Separation of the drug and carrier from the solvent on precipitation can rely on the solubility properties of either the drug or carrier. For example, Simonelli et al, Journal of Pharmaceutical Sciences, Vol. 58, No. 5, May 1969, describes a co-precipitation process wherein sulfathiazole is dissolved in sodium hydroxide, followed by addition of polyvinylpyrrolidone; hydrochloric acid is then added to effect co-precipitation. This process is based on co-precipitation employing the solubility of the drug at different pH values. Such reliance on the solubility of the drug may be problematic in that it is not generally applicable to poorly water soluble drugs, as many such drugs do not exhibit a pH dependent solubility. Florence et al, Communications, J. Pharm. Pharmac., 1976, 28 601, describes co-precipitation of trifluoperazine embonate and the polymers poly DL-aspartic acid and polymethylmethacrylate. The co-precipitates were prepared by dissolving the drug and polymer in dimethylformamide and adding the solution to a rapidly stirred volume of water. Both polymers and drug are insoluble in water.

In general terms, problems which can be associated with known co-precipitation techniques can include excess solvent usage, identifying carrierldrug combinations which can be effectively precipitated and enhance bioavailability, the use of heat to effect solution which may detrimentally affect the drug, and the like. Co-precipitation techniques are however attractive for the preparation of solid dispersions, in that less solvents and heat are employed when compared to techniques such as co-evaporation and solvent removal may therefore be facilitated.

We have now developed a co-precipitation technique which alleviates the above described disadvantages associated with known techniques, and have also found that co-precipitation offers an advantageous preparation route for solid dispersions of poorly water soluble drugs.

There is therefore provided in a first aspect of the present invention a process of preparing a solid dispersion comprising a poorly water soluble drug or salts or solvates (e.g. hydrates) thereof, and a pharmaceutically acceptable carrier or excipient therefor, which process comprises:
  (i) providing an intimate mixture comprising the carrier or excipient and a non-aqueous, water miscible solvent or combination of solvents, and optionally, water;
  (ii) co-mixing the intimate mixture obtained in step (a) with a poorly water soluble drug; and
  (iii) co-precipitating the poorly water soluble drug and the carrier or excipient.

As used herein, the term "intimate mixture" can denote a solution, suspension, emulsion, colloid, dispersion or the like. Generally, the term "intimate mixture" as used herein denotes a solution.

It has been found surprisingly that small amounts of water in the intimate mixture can aid dissolution of the subsequently added poorly water soluble drug. For example, a 10% ratio of water in a solvent may aid dissolution of the poorly water soluble drug.

In a further aspect, the invention describes a process of preparing a solid dispersion comprising a particular cGMP specific PDE (PDEV) inhibitor. More particularly, co-precipitation overcomes problems associated with other preparatory processes for formulating the subject PDEV inhibitor.

There is therefore provided by the present invention a process of preparing a solid dispersion comprising (6R, 12aR)-2,3,6,7,12,12a-Hexahydro-2methyl-6-(3,4-methylenedioxyphenyl)-pyrazino[2',1':6,1]pyrido[3,4-b]indole-1,4-dione (hereinafter referred to as Compound A) or salts or solvates (e.g. hydrates) thereof, and a pharmaceutically acceptable carrier or excipient therefor, which process comprises co-precipitating Compound A and the pharmaceutically acceptable carrier or excipient.

In a yet further aspect, the invention describes a process of preparing a solid dispersion comprising a particular gastrin and CCK-B antagonist. More particularly, co-precipitation overcomes problems associated with other preparatory processes for formulating the subject gastrin and CCK-B antagonist.

There is therefore provided by the present invention a process of preparing a solid dispersion comprising (+)-N-[1-(Adamantanmethyl)-2,4dioxo-5-phenyl-2,3,4,5-tetrahydro-1H-1,5benzodiazepin-3-yl]-N'-phenylurea (hereinafter referred to as Compound B) or salts or solvates (e.g. hydrates) thereof, and a pharmaceutically acceptable carrier or excipient therefor, which process comprises co-precipitating Compound B and the pharmaceutically acceptable carrier or excipient. The synthesis and use of Compound B has been previously described in WO93.14074.

Suitably the co-precipitation of Compound A or B comprises the steps of:

(a) providing an intimate mixture of a poorly water soluble drug selected from Compound A or Compound B, the carrier or excipient therefor and a non-aqueous, water miscible solvent or combination of solvents, and optionally, water; and (b) co-precipitating the compound and the carrier or excipient.

It is generally advantageous in step (a) to first co-mix the carrier or excipient together with the solvent or solvents and optional water, thereby providing an initial intimate mixture, prior to addition of the poorly water soluble drug thereto. Subsequently, the drug can be added to the initial intimate mixture. Optionally, the carrier or excipient and solvent initial intimate mixture can be subjected to heating sufficient to facilitate dissolving of the former in the latter. Such a sequence of steps (also substantially as hereinbefore described according to the first aspect of the present invention) can be beneficial in allowing the employ of heat to effect dissolving, whilst obviating any detrimental affect by the heat on the drug.

A co-precipitation step, substantially as described in step (iii), or substantially as described in step (b), can aptly comprise adding the drug, carrier or excipient and solvent to a co-precipitation medium in which the carrier or excipient is insoluble. The resultant co-precipitate can be separated from the remaining components, suitably by filtering or the like, and the co-precipitate washed to remove residual solvent, and dried. The co-precipitate can then be formulated in a suitable pharmaceutical form employing known formulatory techniques, substantially as hereinafter described.

The carrier or excipient for the drug, and the co-precipitation medium, are respectively chosen so that the carrier or excipient is substantially insoluble in the co-precipitation medium. It is also advantageous that the carrier or excipient has selected dissolution properties in vivo; for example, the carrier or excipient may be such so as to dissolve rapidly (within about 15 to 60 minutes) in vivo, alternatively the carrier or excipient may be such so as to dissolve over a relatively prolonged period of time (typically, 2 to 4 hours) so as to achieve sustained release of drug in vivo.

Suitable carrier or excipients include pharmaceutically acceptable polymeric materials, typical examples being hydroxypropyl methyl cellulose phthalate, polymethylacrylate, hydroxypropyl cellulose and other like carrier or excipient materials. Particularly preferred is hydroxypropyl methyl cellulose phthalate as a carrier or excipient, and there is further provided by the present invention co-precipitates consisting of Compound A and hydroxypropyl methyl cellulose phthalate, and Compound B and hydroxypropyl methyl cellulose phthalate.

Aptly the co-precipitation medium comprises an aqueous medium, which is optimally such that the carrier or excipient is substantially insoluble therein as substantially hereinbefore described.

Conveniently the following combinations of carrier or excipient and co-precipitation medium can be employed in a process according to the present invention:

(a) in the case where the carrier or excipient is hydroxypropyl methyl cellulose phthalate, the co-precipitation medium is suitably a weakly acidic medium (pH in the range of 0.5 to 5.0, typically 0.8 to 2.0), typically 0.5N hydrochloric acid or acetic acid;

(b) in the case where the carrier or excipient is an acid soluble polymethylacrylate, the co-precipitation medium is suitably a neutral or basic medium, (pH in the range 6.0 to 13.0), water or dilute alkali being appropriate representatives of suitable co-precipitation media; and (c) in the case where the carrier or excipient is hydroxypropylcellulose, an appropriate co-precipitation medium is again water, aptly with a temperature of greater than about 40° C., such as 70 to 80° C.

It is of course envisaged that other suitable combinations of carrier or excipient and co-recipitation media may be employed, as will be envisaged by a person skilled in the art. A particularly appropriate combination of carrier or excipient and co-precipitation medium, is hydroxypropyl methyl cellulose phthalate and a dilute acidic medium, substantially as hereinbefore described in point (a) above.

Appropriately, the solvent employed in a process according to the present invention is selected from the group consisting of acetone, methanol, dimethylacetamide, dimethylsulphoxide, dimethylformamide, tetrahydrofuran, and combinations thereof, and optionaly, water, although other suitable solvents could be employed. Generally 9:1 acetone/water, 9:1 tetrahydrofuran/water, or 1:1 acetone/methanol mixtures are employed in a process according to the present invention.

There is still further provided by the present invention a solid dispersion consisting essentially of Compound A or Compound B and a pharmaceutically acceptable carrier or excipient therefor. As a further aspect of the present invention, there is provided hereby a solid dispersion comprising Compound A or Compound B obtainable by a process substantially as hereinbefore described.

It has been shown that Compound A is a potent and selective inhibitor of PDEV. Thus, Compound A is of interest for use in therapy, specifically for the treatment of a variety of conditions where inhibition of PDEV is thought to be beneficial.

As a consequence of the selective PDEV inhibition exhibited, cGMP levels are elevated, which in turn can give rise to beneficial anti-platelet, anti-neutrophil, anti-vasospastic, vasodilatory, natriuretic and diuretic activities as well as potentiation of the effects of endothelium-derived relaxing factor (EDRF), nitrovasodilators, atrial natriuretic factor (ANF), brain natriuretic peptide (BNP), C-type natriuretic peptide (CNP) and endothelium-dependent relaxing agents such as bradykinin, acetylcholine and 5-$HT_1$. Elevated cGMP levels may also mediate relaxation of the corpus cavernosum tissue and consequent penile erection in the teatment of male sexual dysfunction. The solid dispersions of Compound A therefore have utility in the treatment of a number of disorders, including stable, unstable and variant (Prinzmetal) angina, hypertension, pulmonary hypertension, congestive heart failure, renal failure, atherosclerosis, conditions of reduced blood vessel patency (e.g. post-percutaneous transluminal coronary angioplasty), peripheral vascular disease, vascular disorders such as Raynaud's disease, inflammatory diseases, stroke, bronchitis, chronic asthma, allergic asthma, allergic rhinitis, glaucoma, diseases characterised by disorders of gut motility (e.g. irritable bowel syndrome), and symptoms associated with male sexual dysfunction.

It will be appreciated that references herein to treatment extend to prophylaxis as well as treatment of established conditions.

There is thus provided as a further aspect of the invention a solid dispersion of Compound A substantially as hereinbefore described for use in therapy, in particular for use in the treatment of conditions where inhibition of PDEV is of therapeutic benefit.

According to another aspect of the invention, there is provided the use of a solid dispersion of Compound A substantially as hereinbefore described for the manufacture of a medicament for use in therapy, in particular the treatment of conditions where inhibition of P0EV is of therapeutic benefit.

In a further aspect, the invention provides a method of treating conditions where inhibition of PDEV is of therapeutic benefit in a human or non-human animal body which comprises administering to said body a therapeutically effective amount of a solid dispersion of Compound A substantially as hereinbefore described.

For administration to man in the curative or prophylactic treatment of the disorders identified above, oral dosages of Compound A will generally be in the range of from 0.5–800 mg daily for an average adult patient (70 kg). Thus for a typical adult patient, individual tablets or capsules contain from 0.2–400 mg of active compound, in a suitable pharmaceutically acceptable vehicle or carrier, for administration in single or multiple doses, once or several times per day.

Dosages for intravenous, buccal or sublingual administration will typically be within the range of from 0.1–400 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

It has been shown that Compound B is a potent and specific antagonist of gastrin and/or CCK-B. The compound has been shown to be an antagonist of CCK, particularly at CCK-B receptors as demonstrated for example by the compound's ability to inhibit the contractile actions of CCK-4 in the presence of a CCK-A antagonist, in the guinea-pig isolated ileum longitudinal muscle-myenteric plexus.

A solid dispersion of Compound B is therefore useful for the treatment and/or prevention of disorders in mammals, especially humans, where modification of the effects of gastrin or CCK-B is of therapeutic benefit. Thus the solid dispersion of Compound B is useful for the treatment of central nervous system disorders where CCK-B and/or gastrin are involved, for example anxiety disorders (including panic disorder, agoraphobia, social phobia, simple phobia, obsessive compulsive disorders, post traumatic stress disorder, and general anxiety disorder), tardive dyskinesia, depression, Parkinson's disease or psychosis. The solid dispersion of Compound B is also useful for the treatment of gastrointestinal disorders especially those where there is an advantage in lowering gastric acidity. Such disorders include peptic ulceration, reflux oesophagitis and Zollinger Ellison syndrome. It may also be useful for the treatment of gastrointestinal disorders such as irritable bowel syndrome, excess pancreatic secretion, acute pancreatitis, motility disorders, antral G cell hyperplasia, fundic mucosal hyperplasia or gastrointestinal neoplasms. It may also be useful for the treatment of dependency on drugs or substances of abuse and withdrawal, Gilles de la Tourette syndrome, or dysfunction of appetite regulatory systems; as well as the treatment of certain tumours of the lower oesophagus, stomach, intestines and colon. Compounds of the invention are also useful for directly inducing analgesia, or enhancing opiate or non-opiate mediated analgesia, as well as anaesthesia or loss of the sensation of pain.

There is thus provided as a further aspect of the invention a solid dispersion of compound B substantially as hereinbefore defined for use in the treatment of conditions where modification of the effects of gastrin and/or CCK-B is of therapeutic benefit.

According to another aspect the invention provides the use of a solid dispersion of compound B substantially as hereinbefore defined for the manufacture of a medicament for use in therapy, in particular for the treatment of conditions where modification of the effects of gastrin and/or CCK-B is of therapeutic benefit.

According to a further aspect of the invention we provide a method for the treatment of a mammal, including man, in particular in the treatment of conditions where modification of the effects of gastrin and/or CCK-B is of therapeutic benefit which method comprises administering an effective amount of a solid dispersion of Compound B substantially as hereinbefore defined to the patient.

It will be appreciated that the amount of Compound B required for use in treatment will vary with the nature of the condition being treated and the age and the condition of the patient and will be ultimately at the discretion of the attendant physician or veterinarian. In general however doses employed for adult human treatment will typically be in the range of 0.01–2000 mg per day e.g 0.01–500 mg per day.

For human use, a solid dispersion substantially as hereinbefore described will generally be administered in admixture with a pharmaceutical carrier selected with regard to the intended route of administration and standard pharmaceutical practice. For example, the compound may be administered orally in the form of tablets containing excipients such as cellulose or lactose, or in capsules or ovules either alone or in admixture with excipients.

Thus, the invention provides in a further aspect a pharmaceutical composition comprising a solid dispersion substantially as hereinbefore described together with a pharmaceutically acceptable carrier therefor.

There is further provided by the present invention a process of preparing a pharmaceutical composition comprising a solid dispersion substantially as hereinbefore described, which process comprises mixing a solid dispersion substantially as hereinbefore described together with a pharmaceutically acceptable carrier therefor.

A solid dispersion substantially as hereinbefore described may also be used in combination with other therapeutic agents which may be useful in the treatment of the above-mentioned disease states. The invention thus provides, in another aspect, a combination of a solid dispersion substantially as hereinbefore described together with another therapeutically active agent, for simultaneous, separate, or sequential use.

The combination referred to above may conveniently be presented for use in the form of a pharmaceutical formulation and thus pharmaceutical compositions comprising a combination as defined above together with a pharmaceutically acceptable diluent or carrier comprise a further aspect of the invention.

The individual components of such a combination may also be administered either sequentially or simultaneously in separate pharmaceutical formulations.

Appropriate doses of known therapeutic agents for use in combination with a solid dispersion of the invention will be readily appreciated by those skilled in the art.

Compound B may be prepared by any suitable method known in the art, for example as described in WO93.14074.

Compound A may be prepared by any suitable method known in the art, or as substantially hereinafter described in the accompanying Examples.

The synthesis of Compound A and of intermediates useful in the preparation thereof, are illustrated by the following, non-limiting Examples.

INTERMEDIATE 1

(R)-N$^\alpha$-(3,4Methylenedioxyphenylcarbonyl)-tryptophan methyl ester

To a suspension of D-tryptophan methyl ester hydrochloride (10.2 g) in anhydrous $CH_2Cl_2$ (150 ml) cooled at 0° C. was added dropwise triethylamine (12.3 ml). To the resulting solution solid piperonyloyl chloride (8.16 g) was added portionwise at the same temperature, and the mixture was stirred at room temperature for 2 hours. The mixture was washed successively with water, 0.5N hydrochloric acid, water, a saturated aqueous solution of $NaHCO_3$ and again with water. After drying over $Na_2SO_4$ and evaporation of the solvent under reduced presure, the resulting oil on trituration from hot cyclohexane afforded the title compound as a white solid (14.7 g).

mp: 123–124° C.

20°

$[a]_D$=-84.4° (c=1.04, $CHCl_3$).

INTERMEDIATE 2

(R)-N$^\alpha$-(3,4-Methlenedioxyphenylthiocarbonyl)-tryptophan methyl ester

A mixture of Intermediate 1 (14 g) and Lawesson's reagent (9.28 g) in dimethoxyethane (280 ml) was heated at 60° C. under $N_2$ for 16 hours with stirring. The reaction mixture was evaporated to dryness and the resulting oil was dissolved in ethyl acetate, then washed successively with an aqueous saturated solution of $NaHCO_3$ and water and dried over $Na_2SO_4$. The oily residue obtained after evaporation under reduced pressure gave, on trituration from cyclohexane, a yellow powder which was filtered and washed with cooled methanol to afford the title compound (9.74 g).

mp: 129–130° C.

20°

$[a]_D$=-186.8° (c=1.14, $CHCl_3$).

INTERMEDIATE 3

(1R,3R)-Methyl 1,2,3,4-tetrahydro-1-(3,4-methylenedioxyphenyl)-9H-pyrido[3,4-b]indole-3-carboxylate A solution of Intermediate 2 (9 g) and methyl iodide (10 ml) in anhydrous dichloromethane (200 ml) was heated at reflux under an argon atmosphere with protection from light. After 24 hours, the solvent was removed under reduced pressure to give an orange oil which on trituration from hexane gave a solid which was washed with ether and used without further purification in the next step. This compound (13.11 g) was dissolved in methanol (250 ml) and the solution was cooled to -78° C. $NaBH_4$ (0.99 g) was then added by portions and the mixture was stirred at the same temperature for 1 hour. The reaction was quenched by addition of acetone (10 ml) and the solvent was removed under reduced pressure. The residue was dissolved in $CH_2Cl_2$, washed with water and then with brine and dried over $Na_2SO_4$. After evaporation of the solvent, the orange oil gave on trituration from a hot mixture of diethyl ether/cyclohexane an orange powder which was recrystallised from diethyl ether/pentane to afford the title compound as a pale yellow solid (5.15 g).

mp: 154–155° C.

20°

$[a]_D$=+24.4° (c=1.03, CHCl3).

INTERMEDIATE 4

(1R,3R)-Methyl 1,2,3,4-tetrahydro-2-chloroacetyl-(3,4-methylenedioxyphenyl)-9H-pyrido[3,4-b]indole-3-carboxylate Method A To a stirred solution of Intermediate 3 (9.7 g) and $NaHCO_3$ (2.79 g) in anhydrous $CHCl_3$ (200 ml) was added dropwise chloroacetyl chloride (5.3 ml) at 0° C. under $N_2$. The resulting mixture was stirred for 1 hour at the same temperature and diluted with $CHCl_3$ (100 ml). Water (100 ml) was then added dropwise with stirring to the mixture, followed by a saturated aqueous solution of $NaHCO_3$. The organic layer was washed with water until neutrality and dried over $Na_2SO_4$. After evaporation of the solvent under reduced pressure, the oily compound obtained was crystallised from ether to give the title compound as a pale yellow solid (9.95 g).

mp: 233° C.

20°

$[a]_D$=-125.4° (c=1.17, $CHCl_3$).

Method B

Chloroacetyl chloride (4 ml) was added dropwide to a solution of Intermediate 3 (16.1 g) and triethylamine (7 ml) in anhydrous $CH_2Cl_2$ (200 ml) at 0° C. under $N_2$. The solution was stirred at 0° C. for 30 minutes, then diluted with $CH_2Cl_2$ (300 ml ). The solution was washed with water (200 ml ), a saturated aqueous solution of $NaHCO_3$ (300 ml) and brine (400 ml). After drying over $Na_2SO_4$ and evaporation under reduced pressure, the resulting solid was washed with ether (300 ml) to give the title compound as a pale yellow solid (18.3 g).

EXAMPLE 1

(6R 12aR)-2,3,6,7,12,12a-Hexahydro-2-methyl-(3,4-methylenedioxyphenyl)-pyrazino[2',1':6,1]pyrido[3,4-b]indole-1,4dione (Compound A)

To a stirred suspension of Intermediate 4 (12.5 g) in MeOH (400 ml) was added at room temperature a solution of methylamine (33% in EtOH) (13.7 ml) and the resulting mixture was heated at 50° C. under $N_2$ for 14 hours. The solvent was removed under reduced pressure and the residue was dissolved in $CH_2Cl_2$ (1 l). After washing with water (3×500 ml), drying over $Na_2SO_4$ and evaporating to dryness, the white solid obtained was recrystallised from 2-propanol to give the title compound as white needles (7.5 g).

mp: 298–300° C.

$[a]_D^{20°}$=+71.3° (c=0.55, $CHCl_3$).

Elemental analysis ($C_{22}H_{19}N_3O_4$) calculated: C, 67.86; H, 4.92; N, 10.79; found: C, 67.79; H, 4.95; N, 10.61%.

Co-precipitation of Compound A: Hydroxypropyl Methylcellulose Phthalate using Acetone/Water

|  | % |
|---|---|
| Compound A | 25–90 |
| Hydroxypropyl methylcellulose phthalate (HPMCP)* | 10–75 |

*Grades HP55 and HP50.

Compound A (1 g) and HPMCP (1 g) were dissolved in a 9:1 mixture of acetone/water (27 ml). 0.25M Hydrochloric acid (83 ml) was added. The resultant co-precipitate was filtered, washed with water (5×3 ml), dried in vacuo and milled.

Co-Precipitation of Compound A: Hydroxypropyl Methylcellulose Phthalate using Tetrahydrofuran/Water

|  | % |
|---|---|
| Compound A | 25–90 |
| Hydroxypropyl methylcellulose phthalate (HPMCP)* | 10–75 |

*Grades HP55 and HP50.

Compound A (1 g) and HPMCP (1 g) were dissolved in a 9:1 mixture of tetrahydrofuran/water (10 ml) and the resultant solution was added to a solution of glacial acetic acid (2.25 ml) in water (37.7 ml). The resultant precipitate was filtered, washed with water (5×3 ml), dried in vacuo and milled.

Co-Precipitation of Compound B: Hydroxypropyl Methylcellulose Phthalate using Acetone/Methanol

|  | % |
|---|---|
| Compound B | 25–90 |
| Hydroxypropyl methylcellulose phthalate (HPMCP)* | 10–75 |

*Grades HP55 and HP50.

Compound B (0.65 g) and HPMCP (0.65 g) were dissolved in a 1:1 mixture of acetone and methanol (35 ml). 0.5N Hydrochloric acid (50 ml) was added followed by distilled water (50 ml). The resultant precipitate was collected, washed with aqueous hydrochloric acid, filtered, and dried in vacuo.

TABLETS FOR ORAL ADMINISTRATION

Co-precipitates of Compound A: HPMCP and Compound B: HPMCP were formulated as follows:

Compound A: HPMCP co-precipitate was blended with the excipients. The resultant mix was compressed into tablets.

|  | mg/tablet |
|---|---|
| 1. | |
| Compound A: HPMCP co-precipitate | 100.0 |
| Microcrystalline cellulose | 289.2 |
| Colloidal silicon dioxide | 0.8 |
| Crospovidone | 8.0 |
| Magnesium stearate | 2.0 |
| 2. | |
| Compound A: HPMCP co-precipitate | 100.0 |
| Microcrystalline cellulose | 229.2 |
| Lactose (anhydrous) | 52.0 |
| Colloidal silicon dioxide | 0.8 |
| Crospovidone | 16.0 |
| Magnesium stearate | 2.0 |
| 3. | |
| Compound A: HPMCP co-precipitate | 100.0 |
| Microcrystalline cellulose | 249.2 |
| Polyvinyl pyrrolidone | 40.0 |
| Colloidal silicon dioxide | 0.8 |
| Crospovidone | 8.0 |
| Magnesium stearate | 2.0 |
| 4. | |
| Compound A: HPMCP co-precipitate | 100.0 |
| Microcrystalline cellulose | 281.2 |
| Sodium lauryl sulphate | 8.0 |
| Colloidal silicon dioxide | 0.8 |
| Crospovidone | 8.0 |
| Magnesium stearate | 2.0 |
| 5. | |
| Compound A: HPMCP co-precipitate | 100.0 |
| Microcrystalline cellulose | 61.87 |
| Dibasic calcium phosphate anhydrous | 62.00 |
| Croscarmellose Sodium | 10.00 |
| Sodium lauryl sulphate | 5.0 |
| Polyvidone 30 | 9.38 |
| Colloidal silicon dioxide | 0.5 |
| Magnesium stearate | 1.25 |

Compound B: HPMCP co-precipitate was blended with the excipients. The resultant mix was compressed into tablets.

| 1. | mg/tablet |
|---|---|
| Compound B: HPMCP co-precipitate | 10.0 |
| Microcrystalline cellulose | 66.74 |
| Dibasic calcium phosphate anhydrous | 66.74 |
| Croscarmellose sodium | 6.00 |
| Magnesium stearate | 0.53 |

Tablets of other strengths may be prepared by altering the ratio of Compound A or B: HPMCP co-precipitate to the other excipients.

FILM COATED TABLETS

The aforementioned tablet formulations were film coated.

| Coating Suspension | % w/w |
|---|---|
| Opadry white + | 13.2 |
| Purified water | to 100.0* |

*The water did not appear in the final product. The maximum theoretical weight of solids applied during coating was 20 mg/tablet.
+ Opadry white is a proprietary material obtainable from Colorcon Limited, U.K. which contains hydroxypropyl methylcellulose, titanium dioxide and triacetin.

The tablets were film coated using the coating suspension in conventional film coating equipment.

CAPSULES

| 1. | mg/capsule |
|---|---|
| Compound A: HPMCP co-precipitate | 100.0 |
| Lactose | 168.5 |
| Polyvinyl pyrrolidone | 30.0 |
| Magnesium stearate | 1.5 |

The Compound A: HPMCP co-precipitate was blended with the excipients. The mix was filled into size No. 0 hard gelatin capsules using suitable equipment.

| 2. | mg/capsule |
|---|---|
| Compound A: HPMCP co-precipitate | 100.0 |
| Microcrystalline cellulose | 183.5 |
| Sodium lauryl sulphate | 6.0 |
| Crospovidone | 9.0 |
| Magnesium stearate | 1.5 |

The Compound A: HPMCP co-precipitate was blended with the excipients. The mix was filled into size No. 0 hard gelatin capsules using suitable equipment.

| 3. | mg/capsule |
|---|---|
| Compound B: HPMCP co-precipitate | 10.0 |
| Lactose | 90.0 |
| Microcrystalline cellulose | 90.0 |
| Crospovidone | 7.0 |
| Sodium lauryl sulphate | 1.0 |
| Magnesium stearate | 2.0 |

The compound B:HPMCP co-precipitate was blended with the excipients. The mix was filled into size No. 1 hard gelatin capsules using suitable equipment. Other strengths may be prepared by altering the ratio of Compound A or B to excipient, the fill weight and if necessary changing the capsule size.

I claim:

1. A process of preparing a solid dispersion comprising a poorly water soluble drug or salts or solvates thereof, and a pharmaceutically acceptable carrier or excipient therefor, which process comprises:
    (a) providing an intimate mixture comprising: (i) the carrier or excipient and (ii) a neutral, nonaqueous, water miscible solvent or combination of solvents, and optionally, water;
    (a) co-mixing the intimate mixture obtained in step (a) with a poorly water soluble drug to form a mixture; and
    (c) co-precipitating the poorly water soluble drug and the carrier or excipient by admixing the mixture of step (b) and water having a pH of 0.5 to 13.

2. A process as claimed in claim 1, wherein the carrier or excipient is a polymeric material selected from hydroxypropyl methyl cellulose phthalate, polymethylacrylate, and hydroxypropyl cellulose.

3. A process as claimed in claim 1, wherein the water is weakly acidic, neutral, or basic.

4. A process as claimed in claim 1, wherein the nonaqueous, water miscible solvent employed is selected from acetone, methanol, dimethylacetamide, dimethylsulphoxide, dimethylformamide, tetrahydrofuran, and combinations thereof.

5. A process as claimed in claim 1, wherein the poorly water soluble drug is (6R, 12aR)-2,3,6,7,12,12a-hexahydro-2-methyl-6-(3,4-methylenedioxyphenyl)-pyrazino[2',1':6,1]pyrido[3,4-b]indole-1,4-dione.

6. A process as claimed in claim 1, wherein the poorly water soluble drug is (+)-N-[1-(adamantanmethyl)-2,4-dioxo-5-phenyl-2,3,4,5-tetrahydro-1H-1,5benzodiazepin-3-yl]-N'-phenylurea.

7. A process as claimed in claim 5 wherein the solvent employed is selected from acetone and tetrahydrofuran in a 10% aqueous mixture.

8. A process as claimed in claim 6 wherein the solvent employed is a combination of acetone and methanol.

9. A process as claimed in claim 1, wherein the carrier or excipient is hydroxypropyl methyl cellulose phthalate.

10. A process as claimed in claim 9, wherein the water has a pH of 0.5 to 5.

11. A process as claimed in claim 1, wherein the carrier or excipient is hydroxypropylcellulose.

12. A process as claimed in claim 11 wherein the water has a temperature greater than about 40° C.

13. A process as claimed in claim 1, wherein the carrier or excipient is polymethyl acrylate.

14. A process as claimed in claim 13 wherein the water has a pH 6 to 13.

15. A process of preparing a solid dispersion comprising (6R,12aR)-2,3,6,7,12,12a-hexahydro-2-methyl-2-(3,4-methylenedioxyphenyl)-pyrazino-[2',1':6,1]pyrido[3,4-b] indole-1,4-dione or salts or solvates thereof, and a pharmaceutically acceptable carrier or excipient therefor, which process comprises:
    (a) providing an intimate mixture of (6R,12aR)-2,3,6,7,12,12a-hexahydro-2-methyl-6-(3,4-methylenedioxyphenyl)-pyrazine[2'1':6,1]pyrido[3,4-b]-indole-1,4-dione, the carrier or excipient therefor, and a neutral nonaqueous, water miscible solvent or combination of solvents, and optionally, water; and
    (b) admixing the intimate mixture of step (a) and water having a pH of 0.5 to 13 to co-precipitate (6R,12aR)-2,3,6,7,12,-12a-hexahydro-2-methyl-6-(3,4-methylenedioxyphenyl)-pyrazine[2'1':6,1]pyrido[3,4-b]-indole-1,4-dione and the carrier or excipient.

16. A process as claimed in claim 15 wherein the carrier or excipient is hydroxypropyl methyl cellulose phthalate.

17. A process as claimed in claim 15, wherein the water has a pH of 0.5 to 5.

18. A process as claimed in claim 15, wherein the solvent employed is selected from acetone and tetrahydrofuran, in a mixture comprising a 10% ratio of water.

19. A process of preparing a solid dispersion comprising (+)-N-[1-(adamantanmethyl)-2,4-dioxo-5-phenyl-2,3,4,5-tetrahydro-1H-1,5-benzodiazepin-3-yl]-N'-phenylurea or salts or solvates thereof, and a pharmaceutically acceptable carrier or excipient therefor, which process comprises:
    (a) providing an intimate mixture of (+)-N-[1-(adamantanmethyl)-2,4-dioxo-5-phenyl-2,3,4,5-tetrahydro-1H-1,5-benzodiazepin-3-yl]-N'-phenylurea, the carrier or excipient therefor, and a neutral nonaqueous, water miscible solvent or combination of solvents, and optionally, water; and
    (b) admixing the intimate mixture of step (a) and water having a pH of 0.5 to 13 to co-precipitate (+)-N-[1-(adamantanmethyl)-2,4-dioxo-5-phenyl-2,3,4,5-tetrahydro-1H-1,5-benzodiazepin-3-yl]-N'-phenylurea and the carrier or excipient.

20. A process as claimed in claim 19 wherein the carrier or excipient is hydroxypropyl methyl cellulose phthalate.

21. A process as claimed in claim 19, wherein the water has a pH of 0.5 to 5.

22. A process as claimed in claim 19, wherein the solvent employed is a combination of acetone and methanol.

23. A solid dispersion comprising (6R,12aR)-2,3,6,7,12,12a-hexahydro-2-methyl-6-(3,4-methylenedioxyphenyl)-pyrazino[2',1':6,1]pyrido[3,4-b]indole-1,4-dione and a pharmaceutically acceptable carrier or excipient therefor.

24. A method of treating in conditions where inhibition of PDEV is of therapeutic benefit in a human or non-human animal body which comprises administering to said body a therapeutically effective amount of a solid dispersion as claimed in claim 23.

25. A pharmaceutical composition comprising a solid dispersion as claimed in claim 23, together with a pharmaceutically acceptable carrier therefor.

26. A process of preparing a pharmaceutical composition comprising a solid dispersion as claimed in claim 23, which process comprises mixing said solid dispersion with a pharmaceutically acceptable carrier therefor.

27. A combination of a solid dispersion as claimed in claim 23, together with another therapeutically active agent, for simultaneous, separate, or sequential use.

28. A pharmaceutical composition comprising a combination as claimed in claim 27 together with a pharmaceutically acceptable diluent or carrier.

* * * * *

UNITED STATES PATENT AND TRADEMARK OFFICE
CERTIFICATE OF CORRECTION

PATENT NO.: 5,985,326
DATED: November 16, 1999
INVENTOR: James Matthew Butler

It is certified that error appears in the above-identified patent and that said Letters Patent is hereby corrected as shown below:

Column 2, line 28, replace "carrier1drug" with "carrier/drug".

Column 4, line 35, replace "co-recipitation" with "co-precipitation".

Column 5, line 31, replace "P0EV" with "PDEV".

Column 7, line 51, replace "(3,4-methlene . . ." with "(3,4-methylene . . .".

Column 8, line 61, replace "(6R 12aR)" with "(6R, 12aR)".

Column 8, line 61, replace, ". . .-2-methyl-(3,4- . . ." with ". . .-2-methyl-6-(3,4- . . ."

Signed and Sealed this

Twenty-second Day of May, 2001

Attest:

NICHOLAS P. GODICI

Attesting Officer

Acting Director of the United States Patent and Trademark Office